United States Patent [19]

Takemi

[11] Patent Number: 5,530,732
[45] Date of Patent: Jun. 25, 1996

[54] METHOD AND APPARATUS FOR EVALUATING THIN-FILM MULTILAYER STRUCTURE

[75] Inventor: Masayoshi Takemi, Itami, Japan

[73] Assignee: Mitsubishi Denki Kabushiki Kaisha, Tokyo, Japan

[21] Appl. No.: 446,061

[22] Filed: May 19, 1995

[30] Foreign Application Priority Data

May 24, 1994 [JP] Japan .................................. 6-109620

[51] Int. Cl.⁶ .................................................. G01N 23/20
[52] U.S. Cl. .................................. 378/73; 378/71; 378/83
[58] Field of Search ............................... 378/71, 73, 83, 378/86, 88, 89

[56] References Cited

U.S. PATENT DOCUMENTS 5,442,676 8/1995 Fewster ................................... 378/73

Primary Examiner—Don Wong
Attorney, Agent, or Firm—Leydig, Voit & Mayer

[57] ABSTRACT

A method of determining the compositions and thicknesses of metamorphic layers at heterointerfaces of periodic laminated structures, such as multiple quantum well structures. An X-ray diffraction pattern of the actual structure is measured and a theoretical X-ray diffraction pattern is calculated using dynamic X-ray theory and giving special attention to X-ray diffraction fringes near a satellite peak in the pattern. The thicknesses and compositions of the metamorphic layers are adjusted in a recursive analysis until the calculated pattern agrees with the measured pattern, thereby providing an accurate analysis of laminated periodic structures.

4 Claims, 7 Drawing Sheets

Fig.1 enlarged view of MQW

METHOD AND APPARATUS FOR EVALUATING THIN-FILM MULTILAYER STRUCTURE

FIELD OF THE INVENTION

The present invention relates to a method and an apparatus for evaluating a thin-film multilayer structure comprising periodically laminated thin films and, more particularly, to a method and an apparatus for quantitatively evaluating fluctuations in composition and thickness of metamorphic layers generated at heterointerfaces in a thin-film multilayer structure with respect to interference fringes produced around a satellite peak in an X-ray diffraction pattern of the multilayer structure.

BACKGROUND OF THE INVENTION

In recent years, it was proved theoretically and experimentally that performance of optical semiconductor devices employed as light sources in optical communication systems and high speed semiconductor devices such as HEMTs in computer systems are significantly improved by employing quantum well structures or superlattice heterostructures. Reduction in thickness and more precise control of chemical composition of layers constituting those structures are important to further improve the devices performance. A promising method for crystal growth to fabricate heterojunction structures and superlattice structures is MOVPE (Metalorganic Vapor Phase Epitaxy). For instance in growth of InGaAs/InP employing this method, trimethylindium (TMI) and triethylgallium (TEG) are decomposed to produce In and Ga atoms, and $AsH_3$ and $PH_3$ are decomposed to produce As and P atoms, whereby an InGaAs layer and an InP layer are epitaxially grown on a substrate. In the MOVPE method of growth of InGaAs/InP, it is difficult to make a steep heterointerface between the InGaAs layer and the InP layer because of a difference in vapor pressure between As and P. Various research organizations have been improving the steepness of the heterointerface utilizing a method of interrupting the growth of the epitaxial layers at the heterointerface. The following (1)–(3) are typical methods for evaluating steepness of the heterointerface:

(1) PL (photoluminescence) measurement (2) Measurement of two-dimensional electron gas mobility (3) X-ray diffraction analysis Although it is possible to macroscopically estimate the thin-film multilayer structure using any of these methods, it is difficult to evaluate respective heterointerfaces of the multilayer structure individually. For instance in the X-ray diffraction analysis which is usually used for evaluating steepness of the heterointerface, in order to evaluate an InGaAs/InP multiquantum well (MQW) structure, a calculated diffraction pattern is fitted to a measured diffraction pattern with respect to:

(1) a difference in diffraction angles between a main peak of X-rays which indicates an average lattice constant of the MQW structure and a peak which indicates the lattice constant of the substrate on which the MQW is grown, and (2) an intensity of a satellite peak which reflects the MQW periodic structure, thereby to compare the design structure and the grown structure, whereby compositions and thicknesses of the metamorphic layers formed at the heterointerfaces are estimated. However, because these compositions and thicknesses of the metamorphic layers estimated by this method are averages of the whole MQW structure, if the MQW structure has minute periodic fluctuations in the compositions and the thicknesses of the metamorphic layers at the respective interfaces, it is difficult to detect those minute fluctuations.

SUMMARY OF THE INVENTION

It is an object of the present invention to provide a method and an apparatus for evaluating fluctuations in compositions and thicknesses of metamorphic layers which are produced at heterointerfaces in an InGaAs/InP MQW structure.

Other objects and advantages of the invention will become apparent from the detailed description that follows. The detailed description and specific embodiments described are provided only for illustration since various additions and modifications within the scope of the invention will be apparent to those skill in the art from the detailed description.

According to a first aspect of the present invention, a method for evaluating a thin-film multilayer structure includes measuring an X-ray diffraction pattern from a thin-film multilayer structure as an object to be measured, which multilayer structure comprises a plurality of thin films which are periodically laminated and including metamorphic layers produced at heterointerfaces, which measurement is carried out including X-ray interference fringes around a satellite diffraction peak;

calculating an X-ray diffraction pattern from a presumed multilayer structure that is obtained on the assumption that periodic metamorphic layers are produced at the respective heterointerfaces of the multilayer structure, on the basis of the dynamic theory of diffraction;

comparing positions of the main diffraction peak and the satellite diffraction peak in the X-ray diffraction pattern measured as described above with those of the X-ray diffraction pattern that is calculated on the basis of the dynamic theory of diffraction, after repeating modification of compositions and thicknesses of the periodic metamorphic layers presumed in the above-described calculation, calculation of the X-ray diffraction patterns, and comparison of the measured X-ray diffraction pattern with the calculated X-ray diffraction pattern, identifying the compositions and the thicknesses of the periodic metamorphic layers presumed in the above-described calculation as the average composition and thickness of the metamorphic layers in the thin-film multilayer structure which is an object to be measured when the positions of the two peaks in the measured X-ray diffraction coincide with those in the calculated X-ray diffraction pattern;

calculating on the basis of the dynamic theory of diffraction, an X-ray diffraction pattern from a presumed thin-film multilayer structure in which it is presumed that the metamorphic layers produced at the respective heterointerfaces have composition fluctuations from the average composition of the metamorphic layers; and comparing the X-ray interference fringes around the satellite diffraction peak in the measured X-ray diffraction pattern from the thin-film multilayer structure with those of the X-ray diffraction pattern which is calculated on the basis of the dynamic theory of diffraction from the presumed thin-film multilayer structure assuming that the metamorphic layers have composition fluctuations at the respective heterointerfaces, after repeating modification of the composition fluctuations of the metamorphic layers which are assumed in the calculation, calculation of the X-ray diffraction patterns, and comparisons of the measured X-ray diffraction pattern with the calculated X-ray diffraction pattern, identifying the composition fluctuations of the periodic metamorphic layers assumed in the above-described calculations as the composition fluctuations of the metamorphic layers in the multilayer structure which is an object to be measured when the interference fringes around the satellite peak in the measured X-ray diffraction pattern coincide with those in the calculated X-ray diffraction pattern. Therefore, the minute fluctuation of the composition of the metamorphic layers which are generated at the heterointerfaces can be evaluated.

According to a second aspect of the present invention, a method for evaluating a thin-film multilayer structure includes measuring an X-ray diffraction pattern from a thin-film multilayer structure as an object to be measured, which multilayer structure comprises a plurality of thin films which are periodically laminated and including metamorphic layers produced at heterointerfaces, which measurement is carried out including X-ray interference fringes around a satellite diffraction peak;

calculating an X-ray diffraction pattern from a presumed multilayer structure that is obtained on the assumption that periodic metamorphic layers are produced at the respective heterointerfaces of the multilayer structure, on the basis of the dynamic theory of diffraction;

comparing positions of the main diffraction peak and the satellite diffraction peak in the X-ray diffraction pattern measured as described above with those of the X-ray diffraction pattern that is calculated on the basis of the dynamic theory of diffraction, after repeating modification of compositions and thicknesses of the periodic metamorphic layers presumed in the above-described calculation, calculation of the X-ray diffraction patterns, and comparison of the measured X-ray diffraction pattern with the calculated X-ray diffraction pattern, identifying the compositions and the thicknesses of the periodic metamorphic layers presumed in the above-described calculation as the average composition and thickness of the metamorphic layers in the thin-film multilayer structure which is an object to be measured when the positions of the two peaks in the measured X-ray diffraction coincide with those in the calculated X-ray diffraction pattern;

calculating on the basis of the dynamic theory of diffraction, an X-ray diffraction pattern from a presumed thin-film multilayer structure in which it is presumed that the metamorphic layers produced at the respective heterointerfaces have thickness fluctuations from the average thickness of the metamorphic layers; and comparing the X-ray interference fringes around the satellite diffraction peak in the measured X-ray diffraction pattern from the thin-film multilayer structure with those of the X-ray diffraction pattern which is calculated on the basis of the dynamic theory of diffraction from the presumed thin-film multilayer structure assuming that the metamorphic layers have thickness fluctuations at the respective heterointerfaces, after repeating modification of the thickness fluctuations of the metamorphic layers which are assumed in the calculation, calculation of the X-ray diffraction patterns, and comparisons of the measured X-ray diffraction pattern with the calculated X-ray diffraction pattern, identifying the thickness fluctuations of the periodic metamorphic layers assumed in the above-described calculations as the thickness fluctuations of the metamorphic layers in the multilayer structure which is an object to be measured when the interference fringes around the satellite peak in the measured X-ray diffraction pattern coincide with those in the calculated X-ray diffraction pattern. Therefore, the minute fluctuation of the thickness of the metamorphic layers which are generated at the heterointerfaces can be evaluated.

According to a third aspect of the present invention, an apparatus for evaluating a thin-film multilayer structure includes:

means for measuring an X-ray diffraction pattern from a thin-film multilayer structure as an object to be measured, which multilayer structure comprises a plurality of thin films that are periodically laminated and includes metamorphic layers produced at heterointerfaces, which measurement is carried out including interference fringes around a satellite peak;

means for temporarily setting compositions and thicknesses of periodic metamorphic layers on the assumption that the periodic metamorphic layers are produced at the heterointerfaces in the multilayer structure;

means for temporarily setting composition fluctuations of the metamorphic layers which are assumed to be produced at the respective heterointerfaces in the design multilayer structure, on the assumption that the metamorphic layers have composition fluctuations from an average composition;

means for calculating an X-ray diffraction pattern from a presumed thin-film multilayer structure determined by setting parameters including compositions and thicknesses of the periodically laminated thin films constituting the multilayer structure, average compositions and thicknesses of the periodic metamorphic layers, and composition fluctuations of the metamorphic layers on the basis of the dynamic theory of diffraction; and means for comparing the measured X-ray diffraction pattern with the X-ray diffraction pattern that is calculated on the basis of the dynamic theory of diffraction, and sending the means for temporarily setting compositions and thicknesses of the metamorphic layers a signal to make that means again set compositions and thicknesses of the metamorphic layers when the compositions and thicknesses of the periodic metamorphic layers are set, the composition fluctuations of the metamorphic layers are not set, and positions of the main diffraction peak and the satellite diffraction peak in the measured diffraction pattern do not coincide with positions of the main diffraction peak and the satellite diffraction peak in the calculated diffraction pattern, identifying the compositions and the thicknesses of the assumed periodic metamorphic layers in the above-described calculations as average composition and thickness of the metamorphic layers in the thin-film multilayer structure which is an object to be measured and, thereafter, sending the means for temporarily setting composition fluctuations of the metamorphic layers a signal to make that means set composition fluctuations of the metamorphic layers when the compositions and the thicknesses of the periodic metamorphic layers are set, the composition fluctuations of the metamorphic layers are not set, and positions of the main diffraction peak and the satellite diffraction peak in the measured diffraction pattern coincide with positions of the main diffraction peak and the satellite diffraction peak in the calculated diffraction pattern, sending the means for temporarily setting composition fluctuations of the metamorphic layers a signal to make that means again set composition fluctuations of the metamorphic layers when the compositions and the thicknesses of the assumed periodic metamorphic layers are identified as average composition and thickness of the metamorphic layers in the thin-film multilayer structure which is an object to be measured, the composition fluctuations of the metamorphic layers are set, positions of the main diffraction peak and the satellite diffraction peak in the measured diffraction pattern coincide with positions of the main diffraction peak and the satellite diffraction peak in the calculated diffraction pattern, and interference fringes around the satellite peak in the measured diffraction pattern do not coincide with interference fringes around the satellite peak in the calculated diffraction pattern, identifying the set composition fluctuations of the metamorphic layers employed in calculating the diffraction pattern as composition fluctuations of the metamorphic layers in the thin-film multilayer structure which is an object to be measured when the compositions and the thicknesses of the assumed periodic metamorphic layers are identified as average composition and thickness of the metamorphic layers in the thin-film multilayer structure which is an object to be measured, the composition fluctuations of the metamorphic layers are set, positions of the main diffraction peak and the satellite diffraction peak in the measured diffraction pattern coincide with positions of the main diffraction peak and the satellite diffraction peak in the calculated diffraction pattern, and the interference fringes around the satellite peak in the measured diffraction pattern coincide with the interference fringes around the satellite peak in the calculated diffraction pattern. Therefore, an apparatus for evaluating minute fluctuations of the composition of the metamorphic layers at the heterointerfaces can be constructed.

According to a fourth aspect of the present invention, an apparatus for evaluating a thin-film multilayer structure includes;

means for measuring an X-ray diffraction pattern from a thin-film multilayer structure as an object to be measured, which multilayer structure comprises a plurality of thin films that are periodically laminated and includes metamorphic layers produced at heterointerfaces, which measurement is carried out including interference fringes around a satellite peak;

means for temporarily setting compositions and thicknesses of periodic metamorphic layers on the assumption that the periodic metamorphic layers are produced at the heterointerfaces in the multilayer structure;

means for temporarily setting thickness fluctuations of the metamorphic layers which are assumed to be produced at the respective heterointerfaces in the design multilayer structure, on the assumption that the metamorphic layers have thickness fluctuations from an average thickness mentioned later;

means for calculating an X-ray diffraction pattern from a presumed thin-film multilayer structure determined by setting parameters including compositions and thicknesses of the periodically laminated thin films constituting the multilayer structure, average compositions and thicknesses of the periodic metamorphic layers, and thickness fluctuations of the metamorphic layers on the basis of the dynamic theory of diffraction; and means for comparing the measured X-ray diffraction pattern with the X-ray diffraction pattern that is calculated on the basis of the dynamic theory of diffraction, and sending the means for temporarily setting compositions and thicknesses of the metamorphic layers a signal to make that means again set compositions and thicknesses of the metamorphic layers when the compositions and thicknesses of the periodic metamorphic layers are set, the thickness fluctuations of the metamorphic layers are not set, and positions of the main diffraction peak and the satellite diffraction peak in the measured diffraction pattern do not coincide with positions of the main diffraction peak and the satellite diffraction peak in the calculated diffraction pattern, identifying the compositions and the thicknesses of the assumed periodic metamorphic layers in the above-described calculations as average composition and thickness of the metamorphic layers in the thin-film multilayer structure which is an object to be measured and, thereafter, sending the means for temporarily setting thickness fluctuations of the metamorphic layers a signal to make that means set thickness fluctuations of the metamorphic layers when the compositions and the thicknesses of the periodic metamorphic layers are set, the thickness fluctuations of the metamorphic layers are not set, and positions of the main diffraction peak and the satellite diffraction peak in the measured diffraction pattern coincide with positions of the main diffraction peak and the satellite diffraction peak in the calculated diffraction pattern, sending the means for temporarily setting thickness fluctuations of the metamorphic layers a signal to make that means again set thickness fluctuations of the metamorphic layers when the compositions and the thicknesses of the assumed periodic metamorphic layers are identified as the average composition and thickness of the metamorphic layers in the thin-film multilayer structure which is an object to be measured, the thickness fluctuations of the metamorphic layers are set, positions of the main diffraction peak and the satellite diffraction peak in the measured diffraction pattern coincide with positions of the main diffraction peak and the satellite diffraction peak in the calculated diffraction pattern, and interference fringes around the satellite peak in the measured diffraction pattern do not coincide with interference fringes around the satellite peak in the calculated diffraction pattern, identifying the set thickness fluctuations of the metamorphic layers employed in calculating the diffraction pattern as thickness fluctuations of the metamorphic layers in the thin-film multilayer structure which is an object to be measured when the compositions and the thicknesses of the assumed periodic metamorphic layers are identified as the average composition and thickness of the metamorphic layers in the thin-film multilayer structure which is an object to be measured, the thickness fluctuations of the metamorphic layers are set, positions of the main diffraction peak and the satellite diffraction peak in the measured diffraction pattern coincide with positions of the main diffraction peak and the satellite diffraction peak in the calculated diffraction pattern, and the interference fringes around the satellite peak in the measured diffraction pattern coincide with the interference fringes around the satellite peak in the calculated diffraction pattern. Therefore, an apparatus for evaluating the minute fluctuations of the thickness of the metamorphic layers at the heterointerfaces can be constructed.

DETAILED DESCRIPTION OF THE PREFERRED EMBODIMENTS

Embodiment 1.

Figure 5:
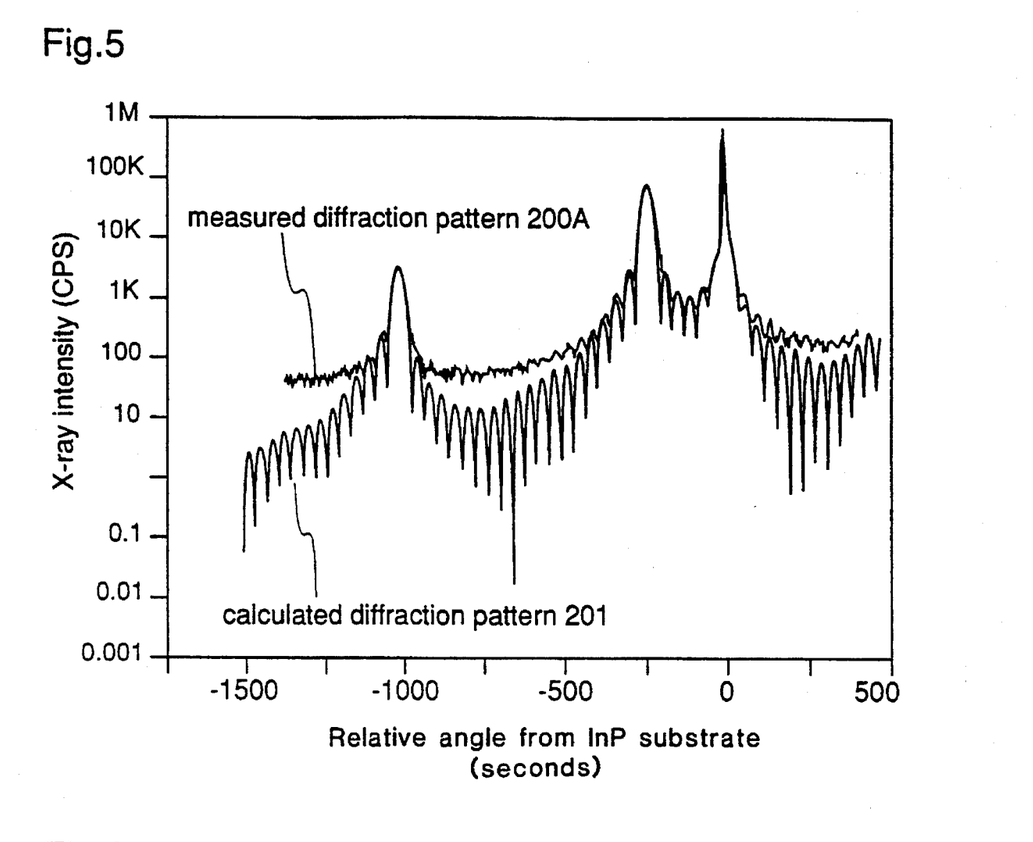
FIG. 5 is an X-ray diffraction pattern calculated on the basis of the dynamic theory of diffraction for the MQW design structure shown in FIG. 1 for which it is assumed that metamorphic layers with fluctuations in composition are produced as shown in FIG. 1, and a measured X-ray diffraction pattern from an MQW structure that is grown on the basis of the design structure, according to the first embodiment of the present invention.
Figure 6:
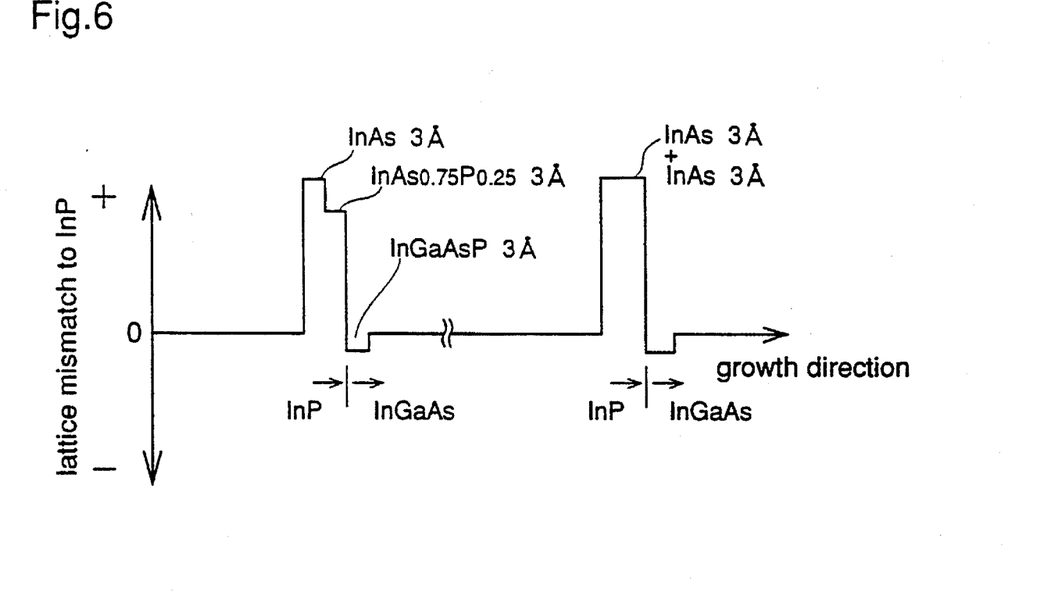
FIG. 6 is a diagram illustrating distribution of lattice mismatch with InP in the film growth direction of the MQW design structure shown in FIG. 1 for which it is assumed that metamorphic layers with fluctuations in composition are produced at heterointerfaces, according to the first embodiment of the present invention.
Figure 7:
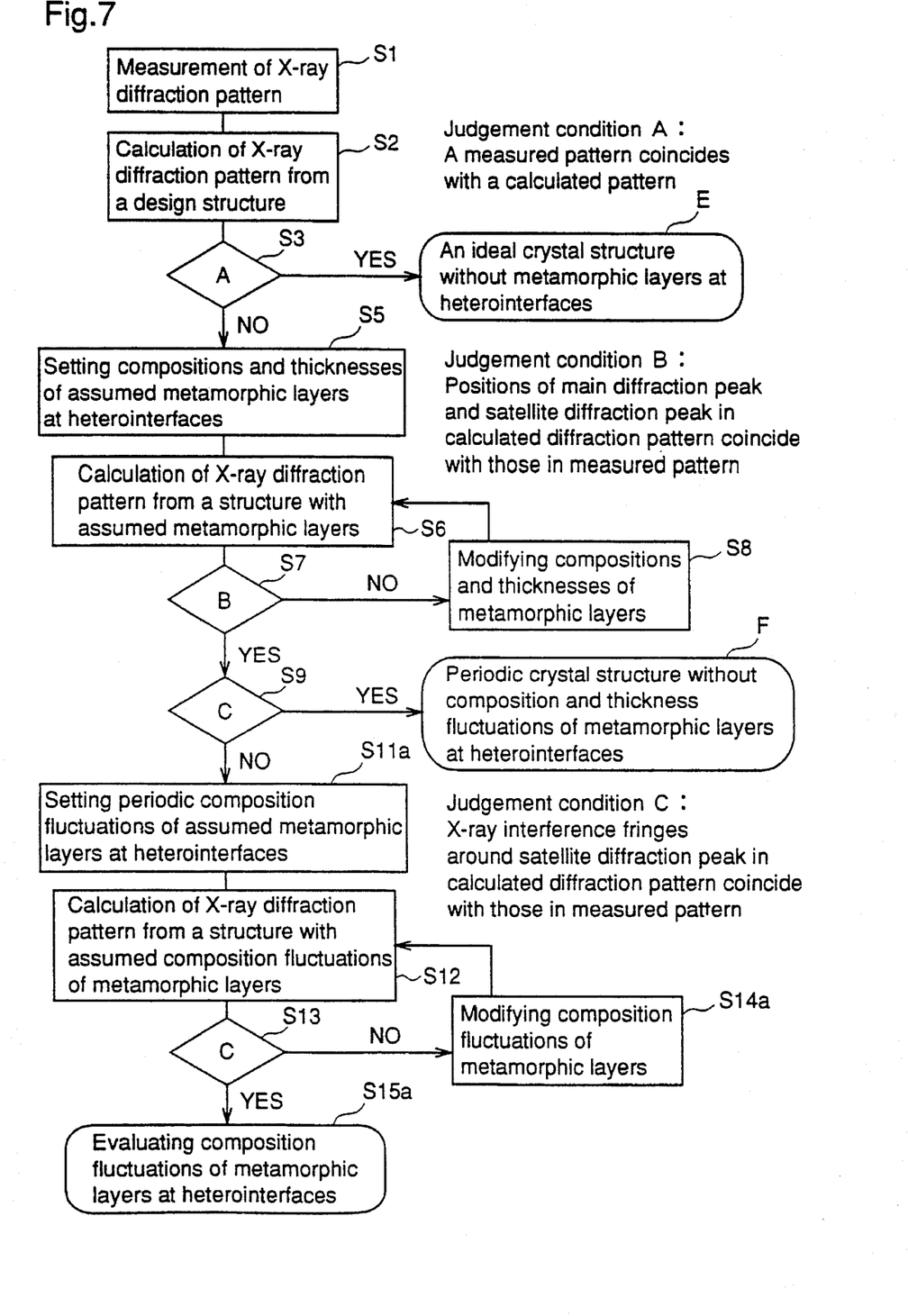
FIG. 7 is a flowchart of a method for quantitatively evaluating fluctuations in composition of the interface metamorphic layers in a thin-film multilayer structure that is carried out by an apparatus for evaluating a multilayer structure according to the first embodiment of the present invention.

A description is given of a method for quantitatively evaluating fluctuations in composition at respective interfaces of a thin-film multilayer structure according to a first embodiment of the present invention with reference to FIGS. 1 to 6 and the flowchart of FIG. 7.

Figure 1:
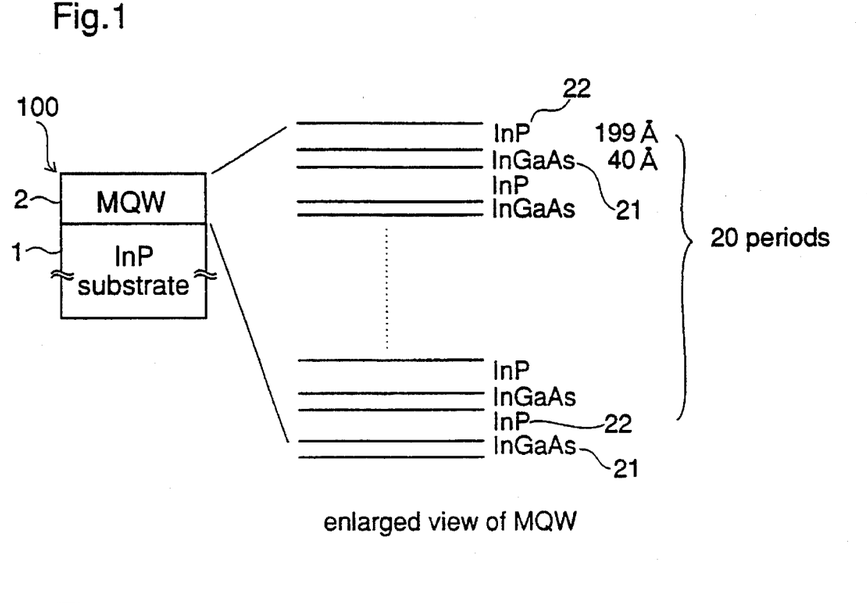
FIG. 1 is a cross-sectional view illustrating an InGaAs/InP-MQW (20 periods) design structure as a target of evaluation in a method of evaluating a thin-film multilayer structure according to a first embodiment of the present invention.

In FIG. 1, reference numeral 1 designates an InP substrate and numeral 2 designates an MQW thin-film multilayer structure grown on the InP substrate 1 by MOVPE. In the MQW multilayer structure 2, twenty InGaAs layers 21 40 Å thick and twenty InP layers 22 199 Å thick are laminated alternatingly as illustrated in FIG. 1. Reference numeral 100 designates a designed structure comprising the InP substrate 1 and the InGaAs/InP-MQW (20 periods) 2.

Figure 2:
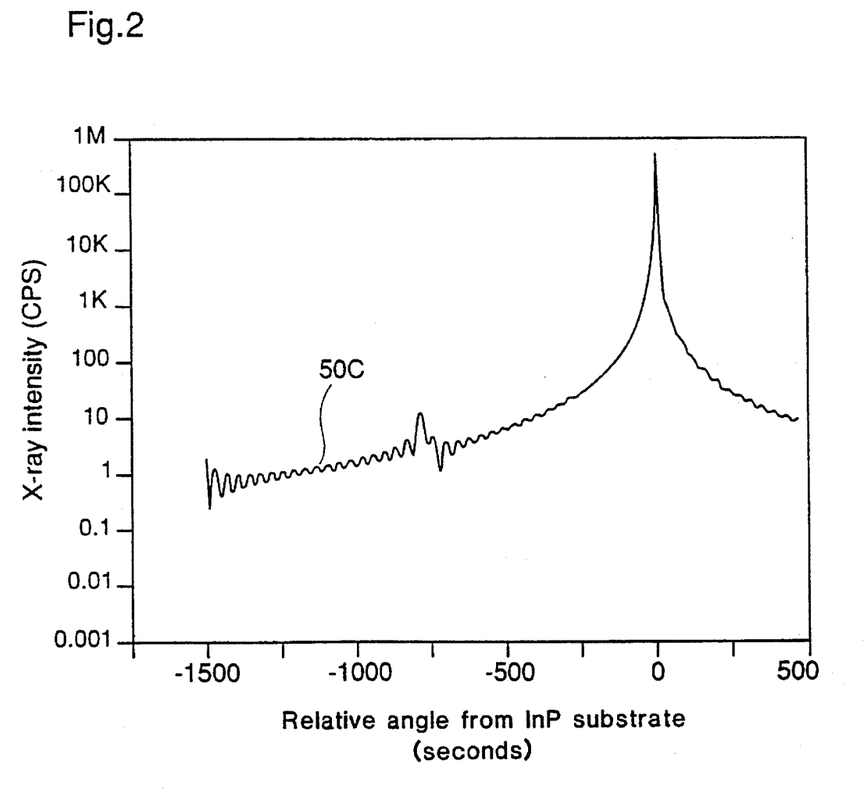
FIG. 2 is a diagram illustrating an X-ray diffraction pattern obtained from the MQW design structure of FIG. 1 and calculated on the basis of the dynamic theory of diffraction according to the first embodiment of the present invention.

FIG. 2 is an X-ray diffraction pattern 50C from the MQW design structure 100 shown in FIG. 1. The pattern is calculated on the basis of the dynamic theory of diffraction.

Figure 3:
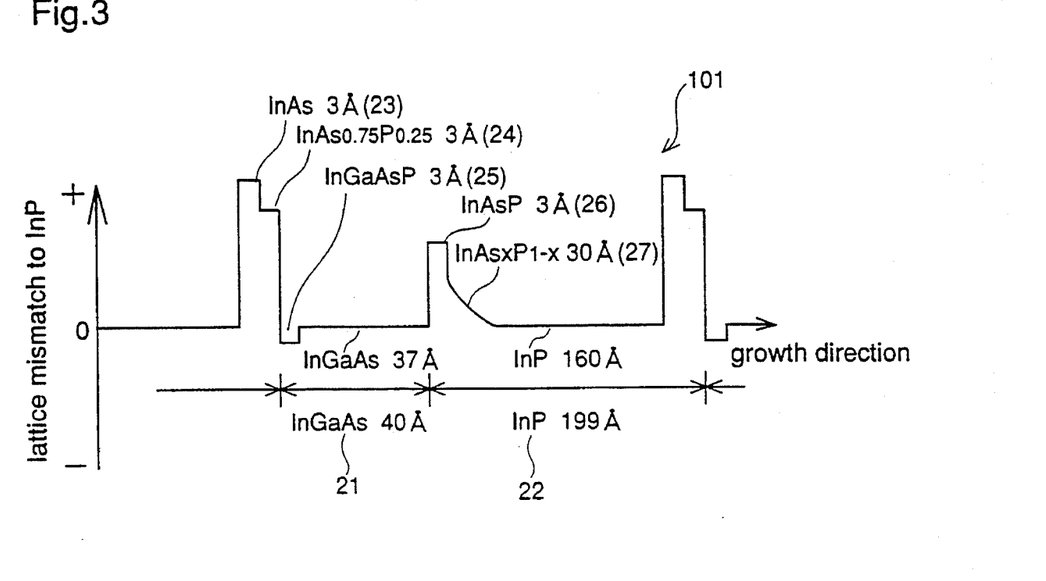
FIG. 3 is a diagram illustrating distribution of lattice mismatch with InP in the film growth direction in the MQW design structure for which it is assumed that metamorphic layers are produced at heterointerfaces, according to the first embodiment of the present invention.

FIG. 3 illustrates a distribution of lattice mismatch relative to InP in the film growth direction in the MQW design structure 100 for which it is assumed that metamorphic layers are produced at heterointerfaces.

Figure 4:
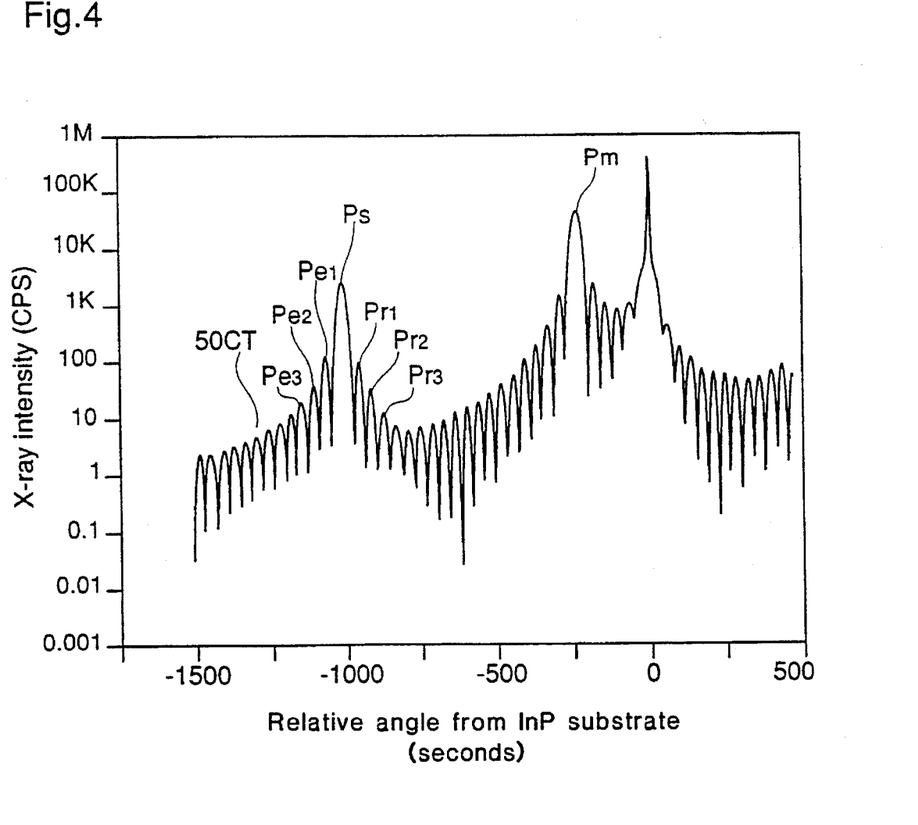
FIG. 4 is an X-ray diffraction pattern calculated on the basis of the dynamic theory of diffraction for the MQW design structure shown in FIG. 1 for which it is assumed that periodic metamorphic layers as shown in FIG. 3 are produced, according to the first embodiment of the present invention.

FIG. 4 is an X-ray diffraction pattern 50CT calculated on the basis of the dynamic theory of diffraction for the MQW design structure 100 for which it is assumed that the periodic metamorphic layers are produced as shown in FIG. 3.

FIG. 5 is an X-ray diffraction pattern calculated on the basis of the dynamic theory of diffraction for the MQW design structure 100 for which it is assumed that metamorphic layers with fluctuations in composition shown in FIG. 6 are produced, and an actually measured X-ray diffraction pattern from an MQW structure that is actually grown on the basis of the design structure 100.

FIG. 6 illustrates a distribution of lattice mismatch relative to InP in the film growth direction in the designed MQW structure 100 for which it is assumed that metamorphic layers with fluctuations in composition are produced at heterointerfaces.

FIG. 7 is a flowchart of a method for quantitatively evaluating fluctuations in composition of the interface metamorphic layers in the multilayer structure, which method is carried out by an apparatus for evaluating the multilayer structure according to the first embodiment of the present invention.

A description is given of the evaluating method according to the first embodiment of the present invention.

(1) An X-ray diffraction pattern, which is obtained from the design structure 100 of FIG. 1 in which the MQW 2 comprising, alternatingly laminated, twenty InGaAs layers and twenty InP layers is disposed on the InP substrate 1, is measured, and the X-ray diffraction pattern 200A shown in FIG. 5 is obtained. Particularly, the X-ray diffraction pattern is measured so as to include a-pattern around a satellite diffraction peak. In addition, the scan speed is reduced so as to perform a precise measurement (step S1).

(2) An X-ray diffraction pattern from the design structure 100 shown in FIG. 1 is calculated on the basis of the dynamic theory of diffraction, and the X-ray diffraction pattern 50C shown in FIG. 2 is obtained (step S2). The dynamic theory of diffraction is the theory of diffraction that considers the incident X-ray is scattered many times in the crystal lattices. In contrast to this theory, there the kinematical theory of diffraction which assumes that the scattering of incident X-ray takes place only once. Since the X-rays diffraction pattern 50C shown in FIG. 2 is calculated for the structure shown in FIG. 1 for which it is assumed that at metamorphic layers are produced, the MQW structure does not have any lattice mismatch with InP substrate. Therefore, a diffraction peak from the InP substrate and diffraction peaks from respective MQW layers on the substrate, the latter overlapping the former, are located at the same position of 0" on the abscissa, and a minute peak reflecting the MQW periodic structure is located at a position of 800" distant from the peak of the substrate on the left hand of the peak. The angle on the abscissa is taken with the InP diffraction angle 31.67° as a reference. Here, 1°=3600".

(3) The measured diffraction pattern 200A and the calculated diffraction pattern 50C are compared. When they coincide with each other (YES at step S3), the sequence proceeds to E shown in FIG. 7 according to the judgment condition A. This means that an ideal crystal structure with no metamorphic layers at heterointerfaces has been obtained. When those two patterns do not coincide, the sequence proceeds to the following (4) (NO at step S3).

(4) Compositions and thicknesses of metamorphic layers which are assumed to be produced at the heterointerfaces are temporarily set as shown in FIG. 3 (step S5), and an X-ray diffraction pattern obtained from the MQW structure including the assumed metamorphic layers is calculated on the basis of the dynamic theory of diffraction (step S6). As a result, an X-ray diffraction pattern 5OCT shown in FIG. 4 is obtained.

(5) Respective positions of the main peak $P_m$ and the satellite peak $P_s$ in the calculated X-ray diffraction pattern 50CT shown in FIG. 4 are compared with those in the measured pattern 200A shown in FIG. 5. When they coincide with each other (YES at step S7), the sequence proceeds to the following (6) according to the judgment condition B shown in FIG. 7. When those positions do not coincide (NO at step S7), the compositions and the thicknesses of the metamorphic layers (reference numerals 23 to 27 in FIG. 3) are modified (step S8) and a new calculation for obtaining a diffraction pattern is carried out using the modified values. Thereafter, the obtained pattern is compared with the measured pattern to carry a judgment in accordance with the judgment condition B. The steps S8, S6, and S7 constituting a loop are repeated until the calculated pattern coincides with the measured pattern.

As a result, an MQW structure which includes metamorphic layers as shown in FIG. 3 is obtained. The structure includes, for example, an InAs layer 23 3 Å thick and an $InAs_{0.75}P_{0.25}$ layer 24 3 Å thick at the terminating side of the InP layer, and an InGaAsP layer 25 3 Å thick at the starting side of the InGaAs layer, and an InAsP layer 26 3 Å thick and an $InAs_xP_{1-x}$ layer 27 30 Å thick at the starting side of InP layer 22. The composition and the thickness of the metamorphic layers can be identified as average compositions and thicknesses of the metamorphic layers in the MQW structure from which the measured X-ray diffraction pattern is obtained. The X-ray diffraction pattern 50CT calculated on the basis of the MQW structure is shown in FIG. 4. Since the X-ray diffraction pattern 50CT shown in FIG. 4 is calculated for the structure shown in FIG. 3 in which the lattice mismatch exists due to the metamorphic layers, a main diffraction peak $P_m$ presenting the average lattice constant in the MQW structure is located at a position −200" from the peak of the InP substrate at 0" on the abscissa, and a satellite diffraction peak $P_s$ presenting a periodic structure of the MQW is located at −1000" from the peak of the substrate. The satellite peak, i.e., the position of −1000", corresponds to the period of the MQW structure, that is, 239 Å which is the sum of the InGaAs layer thickness 40 Å and the InP layer thickness 199 Å.

(6) The X-ray interference fringes $P_{e1}$, $P_{e2}$, $P_{e3}$, ..., $P_{r1}$, $P_{r2}$, $P_{r3}$, ... around the satellite diffraction peak $P_s$ in the calculated diffraction pattern are compared with those in the measured pattern. The number of interference fringes is about 5 or 6 on either side of the satellite peak. When they coincide with each other (YES at step S9), the sequence proceeds to F shown in FIG. 7 according to the judgment condition C shown in FIG. 7. This means that the actual MQW structure has a highly-precise periodic structure with no composition fluctuations in the metamorphic layers at heterointerfaces. When the interference fringes in the calculated diffraction pattern do not coincide with those in the measured pattern (NO at step S9), it is assumed that the metamorphic layers 23–27 at heterointerfaces have appropriate periodic composition fluctuations (step S11a). The composition fluctuations are set temporarily. For instance, as shown in FIG. 6, the metamorphic layers are assumed to include an InAs layer 3 Å thick and a further InAs layer 3 Å thick at the terminating side of the InP layer in the upper three periods of the whole 20 periods of the MQW structure (right side in FIG. 6) and the metamorphic layers in other periods than those three periods are the same as shown in FIG. 3. Then, an X-ray diffraction pattern from the MQW structure including the metamorphic layers with the above-described composition fluctuations is calculated on the basis of the dynamic theory of diffraction (step S12).

(7) When the X-ray interference fringes around the satellite diffraction peak in the calculated diffraction pattern from the structure having the above-described composition fluctuations of the metamorphic layer coincide with those in the measured pattern (YES at step S13), the sequence proceeds to the step S15a according to the judgment condition C. The assumed composition fluctuations of the metamorphic layers then are identified as the composition fluctuations of the actual MQW structure. Thereby, the composition fluctuations in the metamorphic layers at the respective heterointerfaces can be evaluated. When these composition fluctuations do not coincide with each other (NO at step 13), the composition fluctuations of the metamorphic layers at the heterointerfaces are modified (step S14a) and a new calculation for obtaining a diffraction pattern is carried out using the modified fluctuations (step S12). Further, the calculated diffraction pattern and the measured diffraction pattern are compared and judged (step S13). Until the calculated X-ray interference fringes around the satellite diffraction peak coincide with the measured interference fringes, the steps S14a, S12, and S13 constituting a loop are repeated in this order. As a result, the composition fluctuations of the metamorphic layers at the respective heterointerfaces are evaluated (step S15a).

According to the first embodiment of the present invention, the X-ray diffraction pattern 200A is obtained by measuring the X-ray diffraction pattern from the thin-film multilayer structure including the interference fringes around the satellite diffraction peak. The diffraction pattern 50CT is obtained by calculating the X-ray diffraction pattern from the thin-film multilayer structure 101 that is assumed to include the metamorphic layers at the heterointerfaces on the basis of the dynamic theory of diffraction. The calculated diffraction pattern is compared with the measured pattern. When the positions of the main diffraction peak and the satellite diffraction peak in the measured pattern coincide with those in the calculated pattern (judgment condition B), the assumed composition and thickness of the periodic metamorphic layers at the heterointerfaces are identified as the average composition and the average thickness in the actual thin film multilayer structure. Further, an X-ray diffraction pattern from the thin-film multilayer structure including the heterointerface metamorphic layers, which are assumed to have composition fluctuations from the above-described average composition, is calculated on the basis of the dynamic theory of diffraction. Then, the X-ray interference fringes around the satellite diffraction peak in the calculated X-ray diffraction pattern 201 are compared with those of the measured diffraction pattern 200A. When these interference fringes coincide with each other (judgment condition C), the assumed composition fluctuations in the metamorphic layers at the heterointerfaces are identified as composition fluctuations in the metamorphic layers in the actually measured thin film multilayer structure. Consequently, not only the average composition and the average thickness of the metamorphic layers of the thin-film multilayer structure, but also the minute composition fluctuations in the metamorphic layers at the respective heterointerfaces can be quantitatively estimated. That is, the compositions and the thicknesses of the metamorphic layers at the heterointerfaces in the thin-film multilayer structure can be evaluated with high precision.

Embodiment 2.

Figure 8:
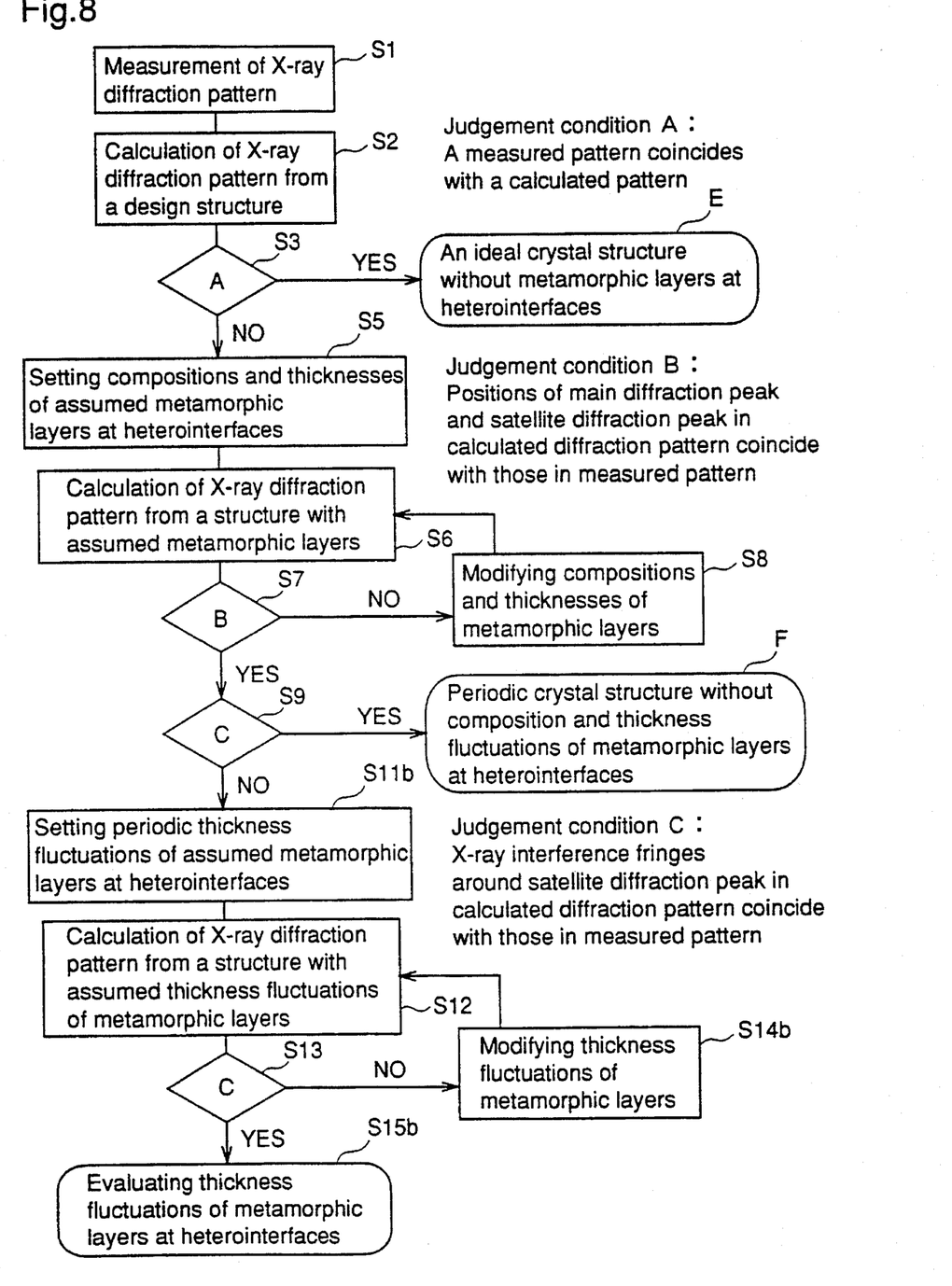
FIG. 8 is a flowchart of a method for quantitatively evaluating fluctuations in thickness of the interface metamorphic layers in a thin-film multilayer structure that is carried out by an apparatus for evaluating a multilayer structure according to a second embodiment of the present invention.

A description is given of a method for quantitatively evaluating fluctuations in thicknesses at respective heterointerfaces in a thin-film multilayer structure according to a second embodiment of the present invention with reference to FIGS. 1 to 4 and a flowchart shown in FIG. 8. The evaluating method shown in FIG. 8 evaluates thickness fluctuations of the metamorphic layers employing a method similar to the evaluating method according to the first embodiment.

(1) An X-ray diffraction pattern from the design structure 100 shown in FIG. 1 in which the MQW 2 comprising, alternatingly laminated, twenty InGaAs layers and twenty InP layers are grown on the InP substrate 1 is measured, and the measured X-ray diffraction pattern 200A shown in FIG. 5 is obtained. Particularly, the X-ray diffraction pattern is measured in a range including the pattern around the satellite diffraction peak. In addition, the scan speed is reduced to perform the measurement with high precision (step S1).

(2) An X-ray diffraction pattern from the design structure 100 shown in FIG. 1 is calculated on the basis of the dynamic theory of diffraction, and the X-ray diffraction pattern 50C shown in FIG. 2 is obtained (step S2). The X-ray diffraction pattern 50C shown in FIG. 2 is the same as that in the description of the first embodiment.

(3) When the calculated diffraction pattern 50C coincides with the measured pattern 200A (YES at step S3), according to the judgment condition A shown in FIG. 8, the sequence proceeds to E shown in FIG. 8, which means that an ideal crystal structure which does not include metamorphic layers at the heterointerfaces is obtained. When those two patterns do not coincide with each other, the evaluation proceeds to the following (4) (NO at step S3).

(4) Appropriate compositions and thicknesses are set for the metamorphic layers formed at the heterointerfaces (at step S5), and the X-ray diffraction pattern obtained from the structure is calculated on the basis of the dynamic theory of diffraction (step S6). The calculated X-ray diffraction pattern 50CT is shown in FIG. 4.

(5) The positions of the main diffraction peak $P_m$ and the satellite diffraction peak $P_s$ in the calculated X-ray diffraction pattern 50CT are compared with those in the measured diffraction pattern 200A (step S7). When these positions coincide with each other (YES at step S7), according to the judgment condition B shown in FIG. 8, the evaluation proceeds to the following (6). When those positions do not coincide with each other (NO at step S7), the compositions and the thicknesses of the metamorphic layers (reference numerals 23–27 in FIG. 3) are modified (step S8), and a new diffraction pattern is calculated using the modified conditions. The new pattern is again compared with the measured pattern and judged according to the judgment condition B. The steps of S8, S6, and S7 constituting a loop are repeated until the calculated pattern coincides with the measured pattern.

As a result, in the same way as in the first embodiment of the invention, a structure of metamorphic layers as shown in FIG. 3 is obtained. The composition and the thickness of the metamorphic layers are identified as the average composition and the average thickness of the metamorphic layers of the thin-film multilayer structure. The X-ray diffraction pattern 50CT calculated on the basis of this structure is shown in FIG. 4.

(6) Then, X-ray interference fringes around the satellite diffraction peak $P_s$ in the calculated diffraction pattern are compared with those in the measured pattern. When these fringes coincide with each other (YES at step S9), according to the judgment condition C shown in FIG. 8, the sequence proceeds to F shown in FIG. 8, which means that a crystal structure having a preferred periodic precision and having no thickness fluctuations of the metamorphic layers at the heterointerfaces is obtained. When these fringes do not coincide with each other (NO at step S9), the metamorphic layers at the heterointerfaces (reference numerals 23–27) are assumed to have periodic thickness fluctuations with respect to the average thickness, and the thickness fluctuations are set temporarily (step S11b). Then, an X-ray diffraction pattern from the structure including the metamorphic layers with those thickness fluctuations is calculated on the basis of the dynamic theory of diffraction (step S12).

(7) The X-ray interference fringes around the satellite diffraction peak in the diffraction pattern that is calculated as one from the structure in which the metamorphic layers have the above-described thickness fluctuations, are compared with those in the measured pattern (step S13). When these fringes coincide with each other (YES at step S13), the sequence proceeds to the step S15b according to the judgment condition C. The set thickness fluctuations of the metamorphic layers are identified as thickness fluctuations of the metamorphic layers of the actual MQW structure, whereby the periodic thickness fluctuations of the heterointerface metamorphic layers are evaluated. When these fringes do not coincide with each other (NO at step S13), the thickness fluctuations of the heterointerface metamorphic layers are modified (step S14b) and the sequence returns to the step S12, i.e., the calculation of the diffraction pattern as described above is carried out. Then, the calculated diffraction pattern is again compared with the measured diffraction pattern and judged at the step S13. Until the X-ray interference fringes around the satellite diffraction peak in the calculated pattern coincide with those in the measured pattern, the steps S14b, S12, and S13 constituting a loop are repeated in this order.

According to the second embodiment of the present invention, the diffraction pattern 200A is obtained by measuring the X-ray diffraction pattern from the thin-film multilayer structure including the interference fringes around the satellite diffraction peak, and the X-ray diffraction pattern 5OCT is obtained by calculating the X-ray diffraction pattern from the thin-film multilayer structure 101 which is assumed to include the metamorphic layers at the heterointerfaces on the basis of the dynamic theory of diffraction. Then, the calculated diffraction pattern 5OCT is compared with the measured pattern 200A. When the positions of the main peak and the satellite peak in the calculated diffraction pattern coincide with those in the measured pattern (judgment condition B), the assumed composition and thickness of the metamorphic layers at the heterointerfaces are identified as the average composition and the average thickness in the actual thin-film multilayer structure. Further, an X-ray diffraction pattern from the thin-film multilayer structure including the heterointerface metamorphic layers which are assumed to have the periodic thickness fluctuations from the average thickness is calculated on the basis of the dynamic theory of diffraction. The calculated X-ray diffraction pattern is compared with the measured pattern 200A for the X-ray interference fringes around the satellite peak. When the interference fringes around the satellite diffraction peak in the calculated diffraction pattern 201 coincide with those in the measured pattern 200A (judgment condition C), the assumed thickness fluctuations of the metamorphic layers at the respective heterointerfaces are identified as the thickness fluctuations of the metamorphic layers in the measured thin-film multilayer structure. Consequently, not only the average composition and the average thickness of the metamorphic layers constituting the MQW structure but also the minute thickness fluctuations of the metamorphic layers can be quantitatively estimated. That is, the compositions and the thicknesses of the metamorphic layers in the multilayer structure can be precisely evaluated.

Embodiment 3.

An apparatus for evaluating a thin-film multilayer structure in accordance with a third embodiment of the present invention comprises the following means, as hardware, for analyzing the composition fluctuations of the metamorphic layers at the heterointerfaces.

Figure 9:
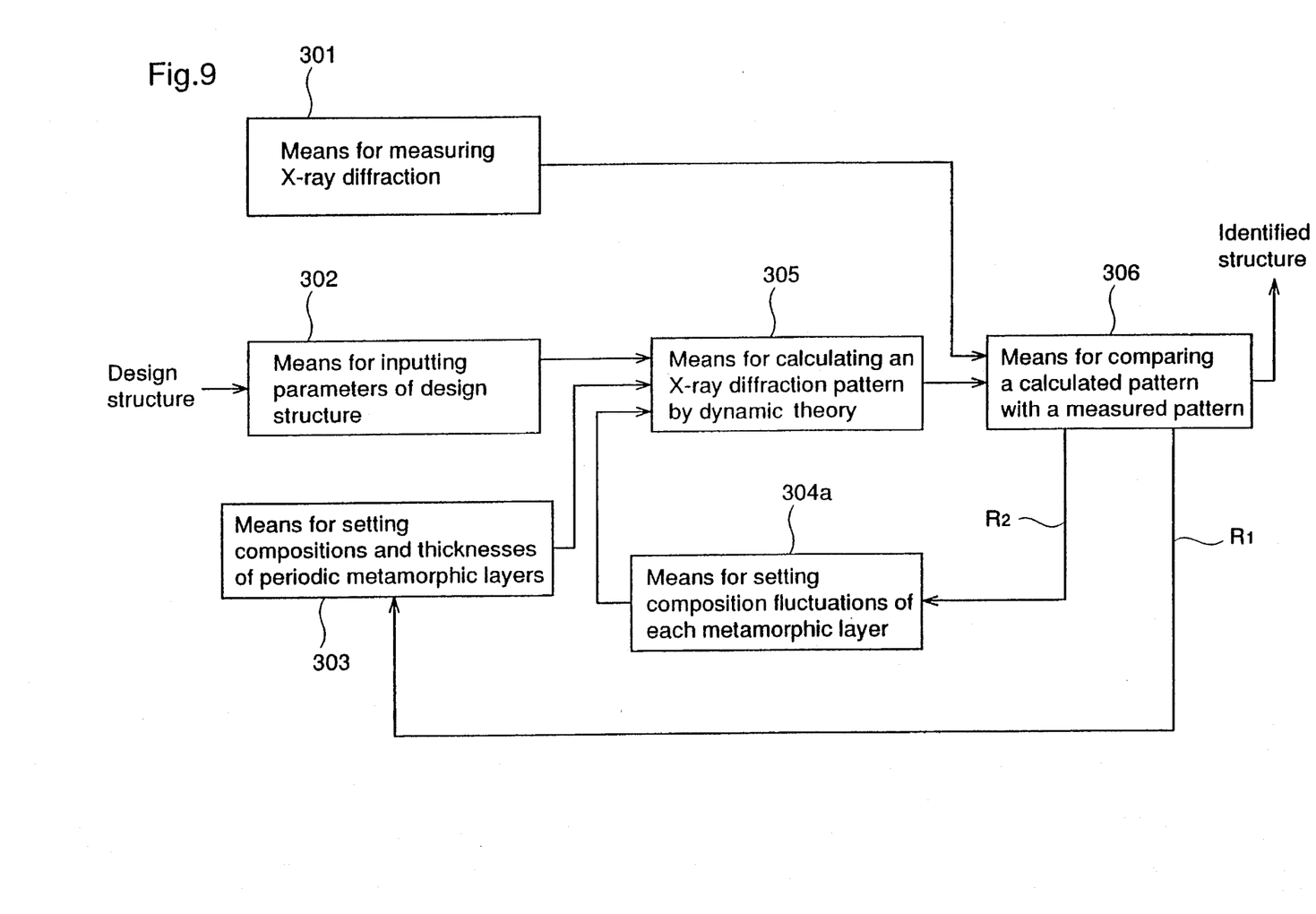
FIG. 9 is a block diagram illustrating an apparatus for quantitatively evaluating fluctuations in composition of interface metamorphic layers in a thin-film multilayer structure according to a third embodiment of the present invention.

The apparatus according to the third embodiment of the invention shown in FIG. 9 comprises the following means.

(1) Means 301 for measuring an X-ray diffraction pattern from a thin-film multilayer structure, which multilayer structure comprises a plurality of periodically arranged thin films that are laminated and include metamorphic layers produced at heterointerfaces, which measurement includes measuring interference fringes around a satellite diffraction peak.

(2) Means 302 for inputting parameters of a design structure of the thin-film multilayer structure.

(3) Means 303 for temporarily setting compositions and thicknesses of periodic metamorphic layers on the assumption that the periodic metamorphic layers are produced at the heterointerfaces in the multilayer structure.

(4) Means 304a for temporarily setting composition fluctuations of the metamorphic layers which are assumed to be produced at the respective heterointerfaces in the design multilayer structure, on the assumption that the metamorphic layers have composition fluctuations from an average composition mentioned later.

(5) Means 305 for calculating an X-ray diffraction pattern from a presumed thin-film multilayer structure determined by setting parameters including compositions and thicknesses of the periodically laminated thin films constituting the multilayer structure, average compositions and thicknesses of the periodic metamorphic layers, and composition fluctuations of the metamorphic layers on the basis of the dynamic theory of diffraction.

(6) Means 306 for comparing the measured X-ray diffraction pattern with the X-ray diffraction pattern that is calculated on the basis of the dynamic theory of diffraction; and sending the means 303 for temporarily setting compositions and thicknesses of the metamorphic layers a signal to make that means again set compositions and thicknesses of the metamorphic layers through a route R1 when the compositions and the thicknesses of the periodic metamorphic layers are set, the composition fluctuations of the metamorphic layers are not set, and positions of the main diffraction peak and the satellite diffraction peak in the measured diffraction pattern do not coincide with positions of the main diffraction peak and the satellite diffraction peak in the calculated diffraction pattern;

identifying the compositions and the thicknesses of the assumed periodic metamorphic layers in the above-described calculations as average composition and thickness of the metamorphic layers in the thin-film multilayer structure which is an object to be measured and, thereafter, sending the means 304a for temporarily setting composition fluctuations of the metamorphic layers a signal to make that means set composition fluctuations of the metamorphic layers through route R2 when the compositions and the thicknesses of the periodic metamorphic layers are set, the composition fluctuations of the metamorphic layers are not set, and positions of the main diffraction peak and the satellite diffraction peak in the measured diffraction pattern coincide with positions of the main diffraction peak and the satellite diffraction peak in the calculated diffraction pattern;

sending the means 304a for temporarily setting composition fluctuations of the metamorphic layers a signal to make that means again set composition fluctuations of the metamorphic layers through route R2 when the compositions and the thicknesses of the assumed periodic metamorphic layers are identified as average composition and thickness of the metamorphic layers in the thin-film multilayer structure, the composition fluctuations of the metamorphic layers are set, positions of the main diffraction peak and the satellite diffraction peak in the measured diffraction pattern coincide with positions of the main diffraction peak and the satellite diffraction peak in the calculated diffraction pattern, and interference fringes around the satellite peak in the measured diffraction pattern do not coincide with interference fringes around the satellite peak in the calculated diffraction pattern; and identifying the set composition fluctuations of the periodic metamorphic layers employed in calculating the diffraction pattern as composition fluctuations of the metamorphic layers in the thin-film multilayer structure when the compositions and the thicknesses of the periodic metamorphic layers are identified as average composition and thickness of the metamorphic layers in the thin-film multilayer structure, the composition fluctuations of the metamorphic layers are set, positions of the main diffraction peak and the satellite diffraction peak in the measured diffraction pattern coincide with positions of the main diffraction peak and the satellite diffraction peak in the calculated diffraction pattern, and the interference fringes around the satellite peak in the measured diffraction pattern coincide with the interference fringes around the satellite peak in the calculated diffraction pattern.

According to the third embodiment of the present invention, the thin film multilayer structure can be automatically evaluated according to the evaluating method of the first embodiment.

Embodiment 4.

An apparatus for evaluating a thin-film multilayer structure in accordance with a fourth embodiment of the present invention comprises the following means as hardware for analyzing the thickness fluctuations of the metamorphic layers at the heterointerfaces.

Figure 10:
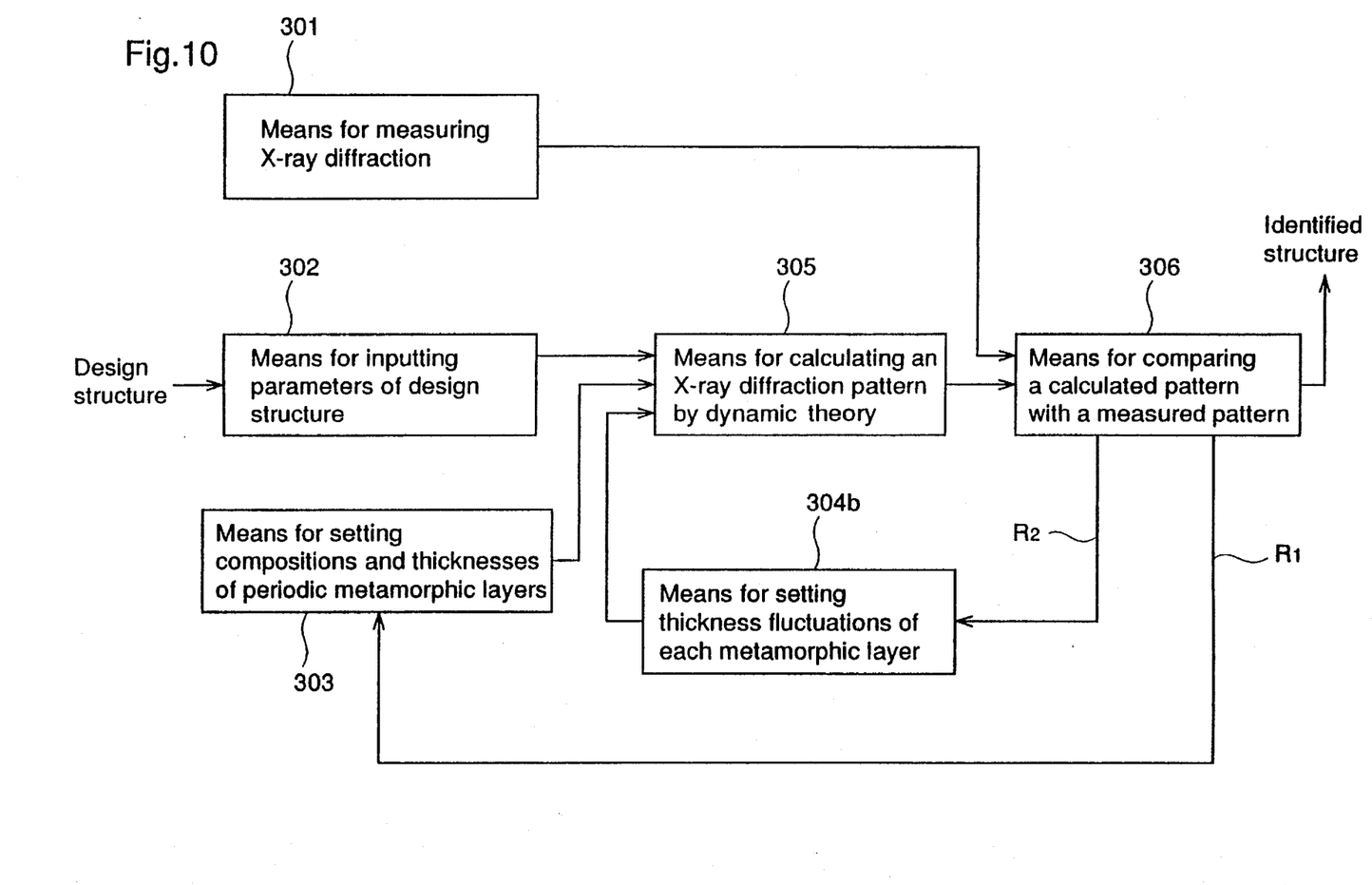
FIG. 10 is a block diagram illustrating a construction of an apparatus for quantitatively evaluating fluctuations in thickness of interface metamorphic layers in the thin-film multilayer structure according to a fourth embodiment of the present invention.

The apparatus according to the fourth embodiment shown in FIG. 10 comprises the following means.

(1) Means 301 for measuring an X-ray diffraction pattern from a thin-film multilayer structure, which multilayer structure comprises a plurality of thin films that are periodically laminated and includes metamorphic layers produced at heterointerfaces, which measurement is carried out including interference fringes around a satellite diffraction peak.

(2) Means 302 for inputting parameters of a design structure of the thin-film multilayer structure.

(3) Means 303 for temporarily setting compositions and thicknesses of periodic metamorphic layers on the assumption that the periodic metamorphic layers are produced at the heterointerfaces in the multilayer structure.

(4) Means 304a for temporarily setting thickness fluctuations of the metamorphic layers which are assumed to be produced at the respective heterointerfaces in the design multilayer structure, on the assumption that the metamorphic layers have composition fluctuations from an average composition mentioned later.

(5) Means 305 for calculating an X-ray diffraction pattern from a presumed thin-film multilayer structure determined by setting parameters including compositions and thicknesses of the periodically laminated thin films constituting the multilayer structure, average compositions and thicknesses of the periodic metamorphic layers, and thickness fluctuations of the metamorphic layers on the basis of the dynamic theory of diffraction.

(6) Means 306 for comparing the measured X-ray diffraction pattern with the X-ray diffraction pattern that is calculated on the basis of the dynamic theory of diffraction; and sending the means 303 for temporarily setting compositions and thicknesses of the metamorphic layers a signal to make that means again set compositions and thicknesses of the metamorphic layers through a route R1 when the compositions and the thicknesses of the periodic metamorphic layers are set, the thickness fluctuations of the metamorphic layers are not set, and positions of the main diffraction peak and the satellite diffraction peak in the measured diffraction pattern do not coincide with positions of the main diffraction peak and the satellite diffraction peak in the calculated diffraction pattern;

identifying the compositions and the thicknesses of the assumed periodic metamorphic layers in the above-described calculations as average composition and thickness of the metamorphic layers in the thin-film multilayer structure and, thereafter, sending the means 304a for temporarily setting composition fluctuations of the metamorphic layers a signal to make that means set composition fluctuations of the metamorphic layers through route R2 when the compositions and the thicknesses of the periodic metamorphic layers are set, the thickness fluctuations of the metamorphic layers are not set, and positions of the main diffraction peak and the satellite diffraction peak in the measured diffraction pattern coincide with positions of the main diffraction peak and the satellite diffraction peak in the calculated diffraction pattern;

sending the means 304a for temporarily setting composition fluctuations of the metamorphic layers a signal to make that means again set composition fluctuations of the metamorphic layers through route R2 when the compositions and the thicknesses of the assumed periodic metamorphic layers are identified as average composition and thickness of the metamorphic layers in the thin-film multilayer structure, the thickness fluctuations of the metamorphic layers are set, positions of the main diffraction peak and the satellite diffraction peak in the measured diffraction pattern coincide with positions of the main diffraction peak and the satellite diffraction peak in the calculated diffraction pattern, and interference fringes around the satellite peak in the measured diffraction pattern do not coincide with interference fringes around the satellite peak in the calculated diffraction pattern;

identifying the set composition fluctuations of the periodic metamorphic layers employed in calculating the diffraction pattern as composition fluctuations of the metamorphic layers in the thin-film multilayer structure when the compositions and the thicknesses of the periodic metamorphic layers are identified as average composition and thickness of the metamorphic layers in the thin-film multilayer structure, the thickness fluctuations of the metamorphic layers are set, positions of the main diffraction peak and the satellite diffraction peak in the measured diffraction pattern coincide with positions of the main diffraction peak and the satellite diffraction peak in the calculated diffraction pattern, and the interference fringes around the satellite peak in the measured diffraction pattern coincide with the interference fringes around the satellite peak in the calculated diffraction pattern.

According to the fourth embodiment of the present invention, the thin film multilayer structure can be automatically evaluated according to the evaluating method of the second embodiment.

What is claimed is:

1. A method for evaluating a thin-film multilayer structure comprising:

measuring an X-ray diffraction pattern from a thin-film multilayer structure, said multilayer structure comprising a plurality of thin films which are periodically laminated and including metamorphic layers produced at heterointerfaces, said measurement including X-ray interference fringes around a satellite diffraction peak;

calculating an X-ray diffraction pattern from a presumed multilayer structure that is obtained on the assumption that periodic metamorphic layers are produced at the respective heterointerfaces of said multilayer structure, on the basis of the dynamic theory of diffraction;

comparing positions of the diffraction peak and the satellite diffraction peak in the X-ray diffraction pattern measured with those of the X-ray diffraction pattern that is calculated on the basis of the dynamic theory of diffraction, after repeating modification of compositions and thicknesses of said periodic metamorphic layers presumed in the calculation, calculation of said X-ray diffraction patterns, and comparison of said measured X-ray diffraction pattern with said calculated X-ray diffraction pattern, identifying the compositions and the thicknesses of said periodic metamorphic layers presumed in the calculation as average composition and thickness of said metamorphic layers in the thin-film multilayer structure when the positions of the two peaks in the measured X-ray diffraction pattern coincide with those in the calculated X-ray diffraction pattern;

calculating, on the basis of the dynamic theory of diffraction, an X-ray diffraction pattern from a presumed thin-film multilayer structure in which it is presumed that said metamorphic layers produced at the respective heterointerfaces have composition fluctuations from the average composition of the metamorphic layers;

comparing X-ray interference fringes around the satellite diffraction peak in the measured X-ray diffraction pattern from the thin-film multilayer structure with those of the X-ray diffraction pattern which is calculated on the basis of the dynamic theory of diffraction from the presumed thin-film multilayer structure assuming that the metamorphic layers have composition fluctuations at the respective heterointerfaces, after repeating modification of the composition fluctuations of said metamorphic layers which are assumed in the calculation, calculation of said X-ray diffraction patterns, and comparison of said measured X-ray diffraction pattern with said calculated X-ray diffraction pattern, identifying the composition fluctuations of said periodic metamorphic layers assumed in the calculations as the composition fluctuations of said metamorphic layers in the multilayer structure when the interference fringes around the satellite peak in the measured X-ray diffraction pattern coincide with those in the calculated X-ray diffraction pattern.

2. A method for evaluating a thin-film multilayer structure comprising:

measuring an X-ray diffraction pattern from a thin-film multilayer structure, said multilayer structure comprising a plurality of thin films which are periodically laminated and including metamorphic layers produced at heterointerfaces, said measurement including X-ray interference fringes around a satellite diffraction peak;

calculating an X-ray diffraction pattern from a presumed multilayer structure that is obtained on the assumption that periodic metamorphic layers are produced at the respective heterointerfaces of said multilayer structure, on the basis of the dynamic theory of diffraction;

comparing positions of the diffraction peak and the satellite diffraction peak in the X-ray diffraction pattern measured with those of the X-ray diffraction pattern that is calculated on the basis of the dynamic theory of diffraction, after repeating modification of compositions and thicknesses of said periodic metamorphic layers presumed in the calculation, calculation of said X-ray diffraction patterns, and comparison of said measured X-ray diffraction pattern with said calculated X-ray diffraction pattern, identifying the compositions and the thicknesses of said periodic metamorphic layers presumed in the calculation as average composition and thickness of said metamorphic layers in the thin-film multilayer structure when the positions of the two peaks in the measured X-ray diffraction pattern coincide with those in the calculated X-ray diffraction pattern;

calculating, on the basis of the dynamic theory of diffraction, an X-ray diffraction pattern from a presumed thin-film multilayer structure in which it is presumed that said metamorphic layers produced at the respective heterointerfaces have thickness fluctuations from the average thickness of the metamorphic layers;

comparing X-ray interference fringes around the satellite diffraction peak in the measured X-ray diffraction pattern from the thin-film multilayer structure with those of the X-ray diffraction pattern which is calculated on the basis of the dynamic theory of diffraction from the presumed thin-film multilayer structure assuming that the metamorphic layers have composition fluctuations at the respective heterointerfaces, after repeating modification of the thickness fluctuations of said metamorphic layers which are assumed in the calculation, calculation of said X-ray diffraction patterns, and comparison of said measured X-ray diffraction pattern with said calculated X-ray diffraction pattern, identifying the thickness fluctuations of said periodic metamorphic layers assumed in the calculations as the thickness fluctuations of said metamorphic layers in the multilayer structure when the interference fringes around the satellite peak in the measured X-ray diffraction pattern coincide with those in the calculated X-ray diffraction pattern.

3. An apparatus for evaluating a thin-film multilayer structure comprising:

means for measuring an X-ray diffraction pattern from a thin-film multilayer structure, which multilayer structure comprises a plurality of thin films that are periodically laminated and includes metamorphic layers produced at heterointerfaces, which measurement includes interference fringes around a satellite diffraction peak;

means for temporarily setting compositions and thicknesses of periodic metamorphic layers on the assumption that the periodic metamorphic layers are produced at the heterointerfaces in the multilayer structure;

means for temporarily setting composition fluctuations of the metamorphic layers which are assumed to be produced at the respective heterointerfaces in a design multilayer structure, on the assumption that the metamorphic layers have composition fluctuations from an average composition;

means for calculating an X-ray diffraction pattern from a presumed thin-film multilayer structure determined by setting parameters including compositions and thicknesses of the periodically laminated thin films constituting the multilayer structure, average compositions and thicknesses of the periodic metamorphic layers, and composition fluctuations of the metamorphic layers on the basis of the dynamic theory of diffraction;

means for comparing the measured X-ray diffraction pattern with the X-ray diffraction pattern that is calculated on the basis of the dynamic theory of diffraction, and sending the means for temporarily setting compositions and thicknesses of the metamorphic layers a signal to make that means again set compositions and thicknesses of the metamorphic layers when the compositions and the thicknesses of the periodic metamorphic layers are set, the composition fluctuations of the metamorphic layers are not set, and positions of the main diffraction peak and the satellite diffraction peak in the measured diffraction pattern do not coincide with positions of the main diffraction peak and the satellite diffraction peak in the calculated diffraction pattern, identifying the compositions and the thicknesses of the assumed periodic metamorphic layers in the calculations as average composition and thickness of said metamorphic layers in the thin-film multilayer structure and, thereafter, sending the means for temporarily setting composition fluctuations of the metamorphic layers a signal to make that means set composition fluctuations of the metamorphic layers when the compositions and the thicknesses of the periodic metamorphic layers are set, the composition fluctuations of the metamorphic layers are not set, and positions of the main diffraction peak and the satellite diffraction peak in the measured diffraction pattern coincide with positions of the main diffraction peak and the satellite diffraction peak in the calculated diffraction pattern, sending the means for temporarily setting composition fluctuations of the metamorphic layers a signal to make that means again set composition fluctuations of the assumed metamorphic layers when the compositions and the thicknesses of the periodic metamorphic layers are identified as average composition and thickness of the metamorphic layers in the thin-film multilayer structure, the composition fluctuations of the metamorphic layers are set, positions of the main diffraction peak and the satellite diffraction peak in the measured diffraction pattern coincide with positions of the main diffraction peak and the satellite diffraction peak in the calculated diffraction pattern, and interference fringes around the satellite peak in the measured diffraction pattern do not coincide with interference fringes around the satellite peak in the calculated diffraction pattern, identifying the set composition fluctuations of the periodic metamorphic layers employed in calculating the diffraction pattern as composition fluctuations of the assumed metamorphic layers in the thin-film multilayer structure when the compositions and the thicknesses of the periodic metamorphic layers are identified as average composition and thickness of the metamorphic layers in the thin-film multilayer structure, the composition fluctuations of the metamorphic layers are set, positions of the main diffraction peak and the satellite diffraction peak in the measured diffraction pattern coincide with positions of the main diffraction peak and the satellite diffraction peak in the calculated diffraction pattern, and the interference fringes around the satellite peak in the measured diffraction pattern coincide with the interference fringes around the satellite peak in the calculated diffraction pattern.

4. An apparatus for evaluating a thin-film multilayer structure comprising:

means for measuring an X-ray diffraction pattern from a thin-film multilayer structure, which multilayer structure comprises a plurality of thin films that are periodically laminated and includes metamorphic layers produced at heterointerfaces, which measurement includes interference fringes around a satellite diffraction peak;

means for temporarily setting compositions and thicknesses of periodic metamorphic layers on the assumption that the periodic metamorphic layers are produced at the heterointerfaces in the multilayer structure;

means for temporarily setting thickness fluctuations of the metamorphic layers which are assumed to be produced at the respective heterointerfaces in a design multilayer structure, on the assumption that the metamorphic layers have thickness fluctuations from an average thickness;

means for calculating an X-ray diffraction pattern from a presumed thin-film multilayer structure determined by setting parameters including compositions and thicknesses of the periodically laminated thin films constituting the multilayer structure, average compositions and thicknesses of the periodic metamorphic layers, and thickness fluctuations of the metamorphic layers on the basis of the dynamic theory of diffraction;

means for comparing the measured X-ray diffraction pattern with the X-ray diffraction pattern that is calculated on the basis of the dynamic theory of diffraction, and sending the means for temporarily setting compositions and thicknesses of the metamorphic layers a signal to make that means again set compositions and thicknesses of the metamorphic layers when the compositions and the thicknesses of the periodic metamorphic layers are set, the thickness fluctuations of the metamorphic layers are not set, and positions of the main diffraction peak and the satellite diffraction peak in the measured diffraction pattern do not coincide with positions of the main diffraction peak and the satellite diffraction peak in the calculated diffraction pattern, identifying the compositions and the thicknesses of the assumed periodic metamorphic layers in the calculations as average composition and thickness of said metamorphic layers in the thin-film multilayer structure and, thereafter, sending the means for temporarily setting thickness fluctuations of the metamorphic layers a signal to make that means set thickness fluctuations of the metamorphic layers when the compositions and the thicknesses of the periodic metamorphic layers are set, the thickness fluctuations of the metamorphic layers are not set, and positions of the main diffraction peak and the satellite diffraction peak in the measured diffraction pattern coincide with positions of the main diffraction peak and the satellite diffraction peak in the calculated diffraction pattern, sending the means for temporarily setting thickness fluctuations of the metamorphic layers a signal to make that means again set thickness fluctuations of the metamorphic layers when the compositions and the thicknesses of the assumed periodic metamorphic layers are identified as average composition and thickness of the metamorphic layers in the thin-film multilayer structure, the thickness fluctuations of the metamorphic layers are set, positions of the main diffraction peak and the satellite diffraction peak in the measured diffraction pattern coincide with positions of the main diffraction peak and the satellite diffraction peak in the calculated diffraction pattern, and interference fringes around the satellite peak in the measured diffraction pattern do not coincide with interference fringes around the satellite peak in the calculated diffraction pattern, identifying the set thickness fluctuations of the periodic metamorphic layers employed in calculating the diffraction pattern as thickness fluctuations of the metamorphic layers in the thin-film multilayer structure when the compositions and the thicknesses of the periodic metamorphic layers are identified as average composition and thickness of said metamorphic layers in the thin-film multilayer structure, the thickness fluctuations of the metamorphic layers are set, positions of the main diffraction peak and the satellite diffraction peak in the measured diffraction pattern coincide with positions of the main diffraction peak and the satellite diffraction peak in the calculated diffraction pattern, and the interference fringes around the satellite peak in the measured diffraction pattern coincide with the interference fringes around the satellite peak in the calculated diffraction pattern.

* * * * *